(12) United States Patent
Lin et al.

(10) Patent No.: US 7,712,192 B2
(45) Date of Patent: May 11, 2010

(54) BELT STRUCTURE

(75) Inventors: Chin-Liang Lin, Taipei (TW);
Shail-Chen Yu, 2F, No.45, Alley5, Lane24, Sec.3, Tingzhou Rd., Taipei City (TW); Chia-Chang Chao, Taipei (TW)

(73) Assignees: Huntex Corporation, Taipei (TW);
Shail-Chen Yu, Taipei (TW)

( * ) Notice: Subject to any disclaimer, the term of this patent is extended or adjusted under 35 U.S.C. 154(b) by 568 days.

(21) Appl. No.: 11/714,772

(22) Filed: Mar. 7, 2007

(65) Prior Publication Data
US 2008/0216213 A1 Sep. 11, 2008

(51) Int. Cl.
*A43C 11/14* (2006.01)
(52) U.S. Cl. ............... 24/70 ST; 24/71 ST; 24/265 BC; 24/265 CD
(58) Field of Classification Search ........................ None
See application file for complete search history.

(56) References Cited

U.S. PATENT DOCUMENTS

| | | | | |
|---|---|---|---|---|
| 4,199,182 A | * | 4/1980 | Sunesson | 24/68 CD |
| 4,542,883 A | * | 9/1985 | Rutzki | 254/217 |
| 6,095,450 A | * | 8/2000 | Jang | 242/388.5 |
| 6,654,987 B1 | * | 12/2003 | Wu | 24/68 CD |
| 7,207,089 B2 | * | 4/2007 | Hanson | 24/68 CD |
| 7,293,760 B1 | * | 11/2007 | Chang | 254/218 |
| 7,510,168 B1 | * | 3/2009 | Lin | 254/218 |
| 2005/0177984 A1 | * | 8/2005 | Huang | 24/68 CD |

FOREIGN PATENT DOCUMENTS

| | | |
|---|---|---|
| TW | M254201 U | 1/2005 |
| TW | M256148 U | 2/2005 |

* cited by examiner

*Primary Examiner*—Jack W. Lavinder
(74) *Attorney, Agent, or Firm*—Muncy, Geissler, Olds & Lowe, PLLC

(57) ABSTRACT

A belt structure includes a first housing, a second housing, a third housing and a belt. The two ends of the belt are respectively connected to the first housing and the third housing, which can be buckled together quickly. The second housing and the first housing are connected, so that a mechanism for fine tuning the belt can be formed through the gear, the driving element and the resisting element in the first and the second housing, thereby a belt structure with fast buckling capability and fine tuning function can be achieved.

17 Claims, 5 Drawing Sheets

BELT STRUCTURE

FIELD OF THE INVENTION

The present invention is related to a belt structure, and more particularly to a belt structure which has the capability of fast buckling and also the function of fine tuning.

BACKGROUND OF THE INVENTION

As first aid, a pressing belt is used to tighten against a human body, for example, during an injury, when the damaged limb might need to be tightened to stop bleeding. When any part of human body has a bleeding cut, it is called an external hemorrhage, such as, an incised wound on the wrist, an abrasion on the face or the lower leg, or a laceration of the arm. The bleeding causes the loss of blood and also the red blood cells, so that the oxygenation function of the human body will be reduced, and if the bleeding becomes very serious or out of control, it might cause shock, even death. Therefore, stopping bleeding undoubtedly is the most important step when processing the injury in an accident. Generally, hemostasis methods may include pressure hemostasis, limb lift hemostasis, and pressure point hemostasis, and the tourniquet hemostasis is the last line of defense for limb hemostasis. The belt used for tourniquet hemostasis should be self-operating, quickly assembled, easily stored and obtained, conveniently adjusting the level of tightness, having a time alarm, combining multiple belts, and be inexpensive.

R.O.C. Patent Publication No. M256148 entitled "Improved tourniquet structure" disposes nylon fasteners located at the inner and outer sides of two ends of an elastic belt to form a tourniquet. However, when adjusting the level of tightness, this kind of tourniquet needs to be loosed first and re-bind again, so that it is inconvenient. Another disclosure is R.O.C Patent Publication No. M254201 entitled "Buckled tourniquet", in which the tourniquet is an elastic belt with a saw plastic plate and a saw shrink box mounted thereon and is fixed through the engagement between the saw plastic plate and the saw shrink box. However, the adjustment of length is still inconvenient and the engagement might also be released by hitting. Therefore, these conventional disclosures still have the drawbacks of unstable engagement structure, uneasily adjusted length and lacking fine tuning capability.

SUMMARY OF THE INVENTION

Consequently, the object of the present invention is to provide a belt which can be fast buckled and has the function of fine tuning.

The present invention provides a belt structure including a first housing, a second housing, a third housing and a belt, wherein one end of the belt is fixed on a hollow axle pipe inside the first housing, and the other end extends through the third housing and is fixed by a pressing shaft, the first housing and the third housing are buckled through an engaging element and a buckling element, thereby a circular belt is formed. The second housing has an axle pillar for extending into the hollow axle pipe of the first housing, so that the second housing can turn by taking the axle pillar and the hollow axle pipe as the axle center. The hollow axle pipe has a gear respectively mounted at two ends thereof, the first housing has at least a resisting element mounted therein, and the second housing has at least a driving element mounted therein, so that through turning the second housing to force the driving element to drive the turning of the gear and through the resisting element disabling the gear from homing, a mechanism for fine tuning the tightness of the belt is achieved. When simultaneously moving the resisting element and the driving element to release the gear, the gear can go back to the original position. Then, through pressing the engaging element of the first housing, the third housing can be departed therefrom, so that a belt with the capability of fast buckling and the function of fine tuning is achieved.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DESCRIPTION OF THE PREFERRED EMBODIMENT

Figure 1:
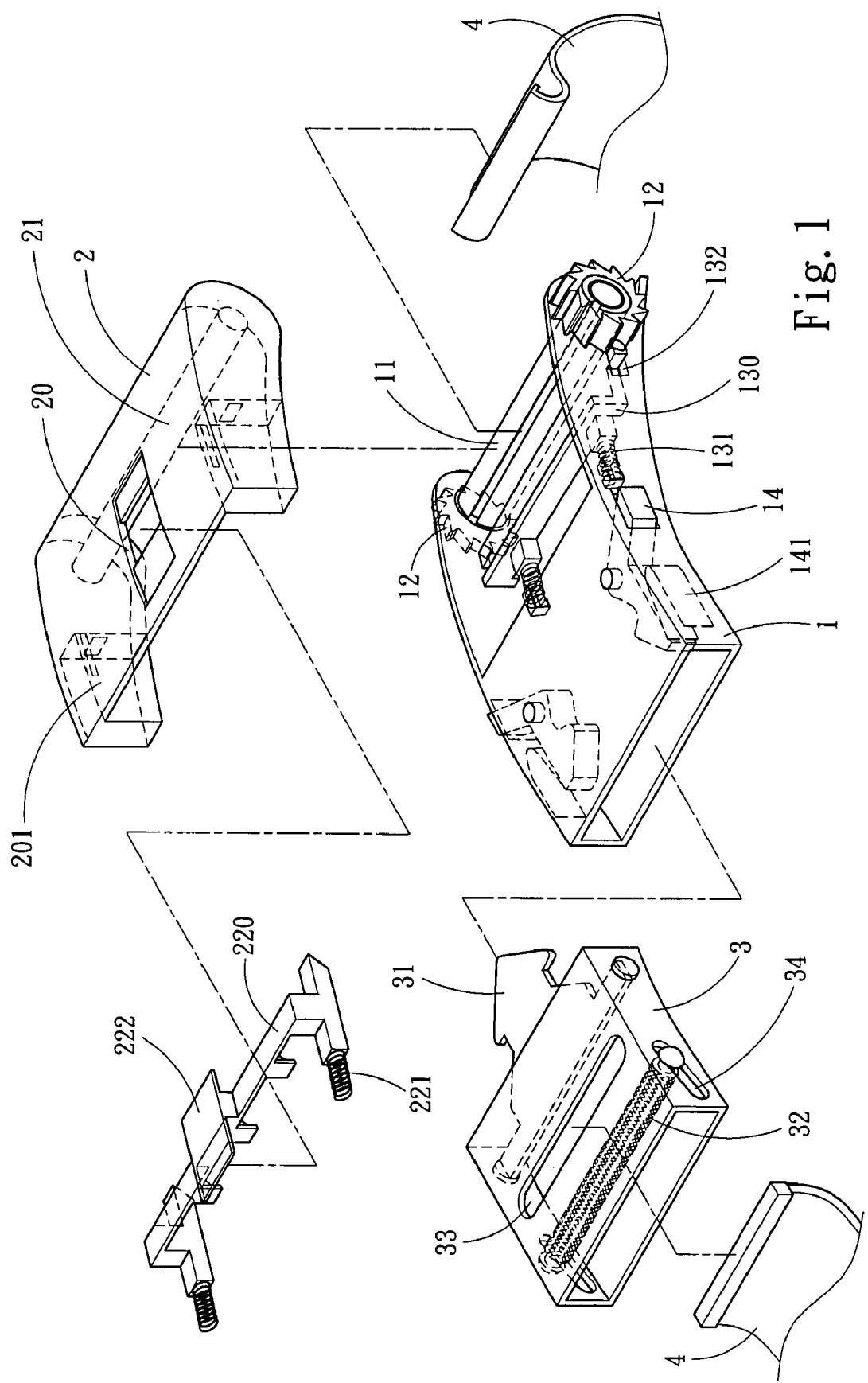
FIG. 1 is a decomposition drawing showing a preferred embodiment according to the present invention.
Figure 2A:
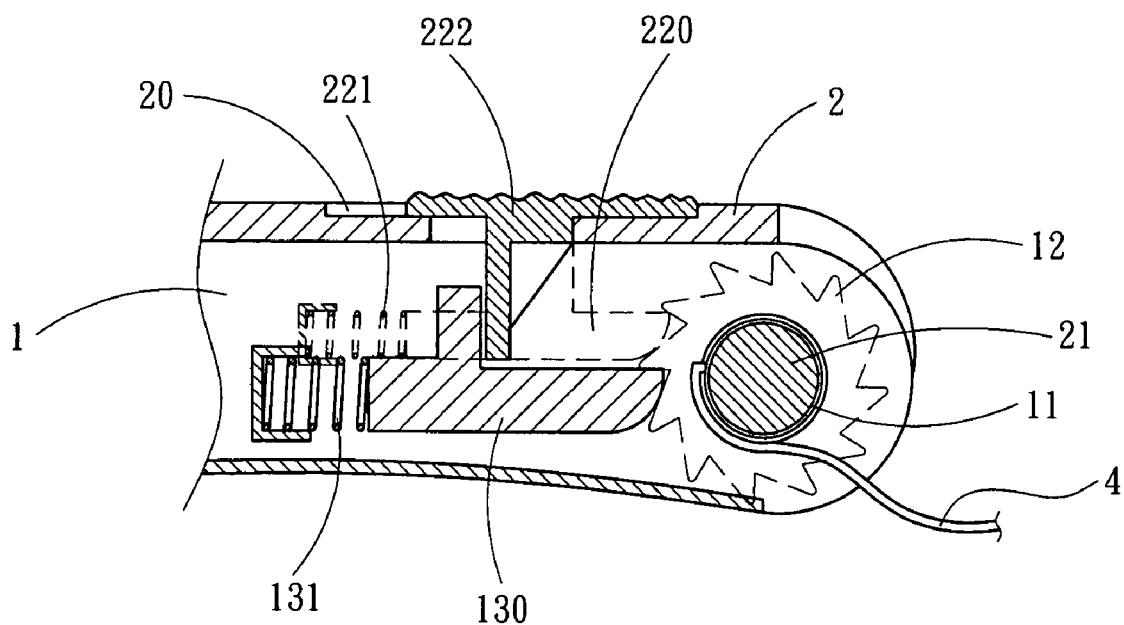
FIGS. 2A to 2D are schematic views showing the fine tuning mechanism according to the present invention.
Figure 2B:
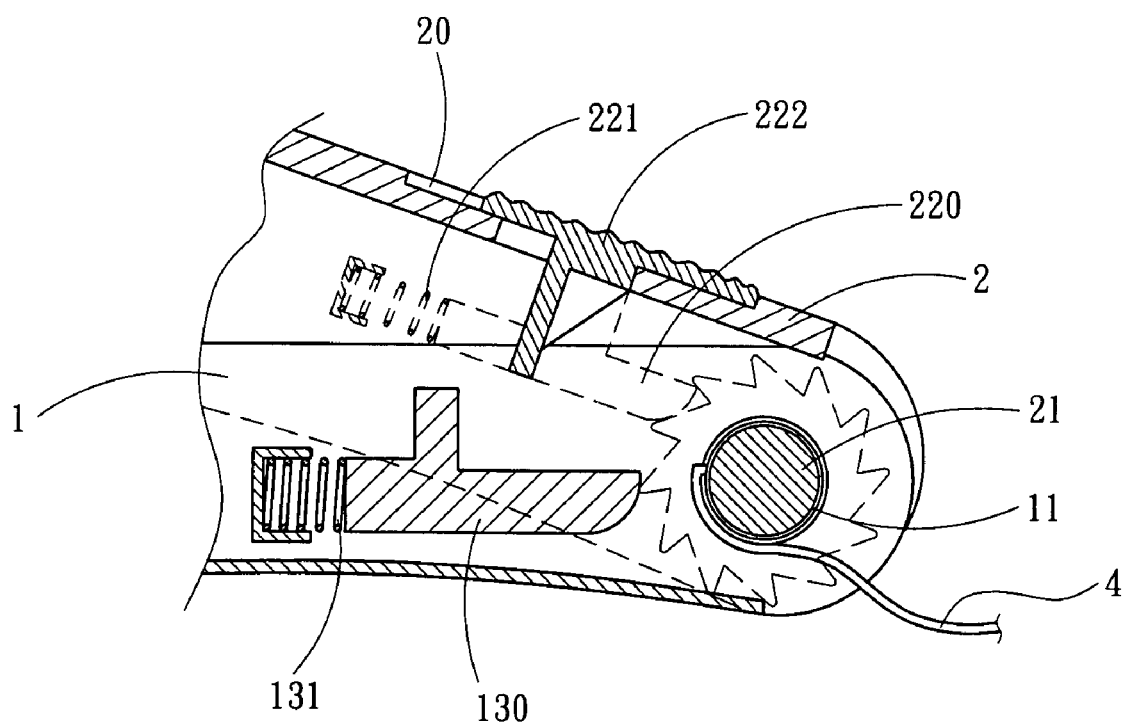
Figure 2C:
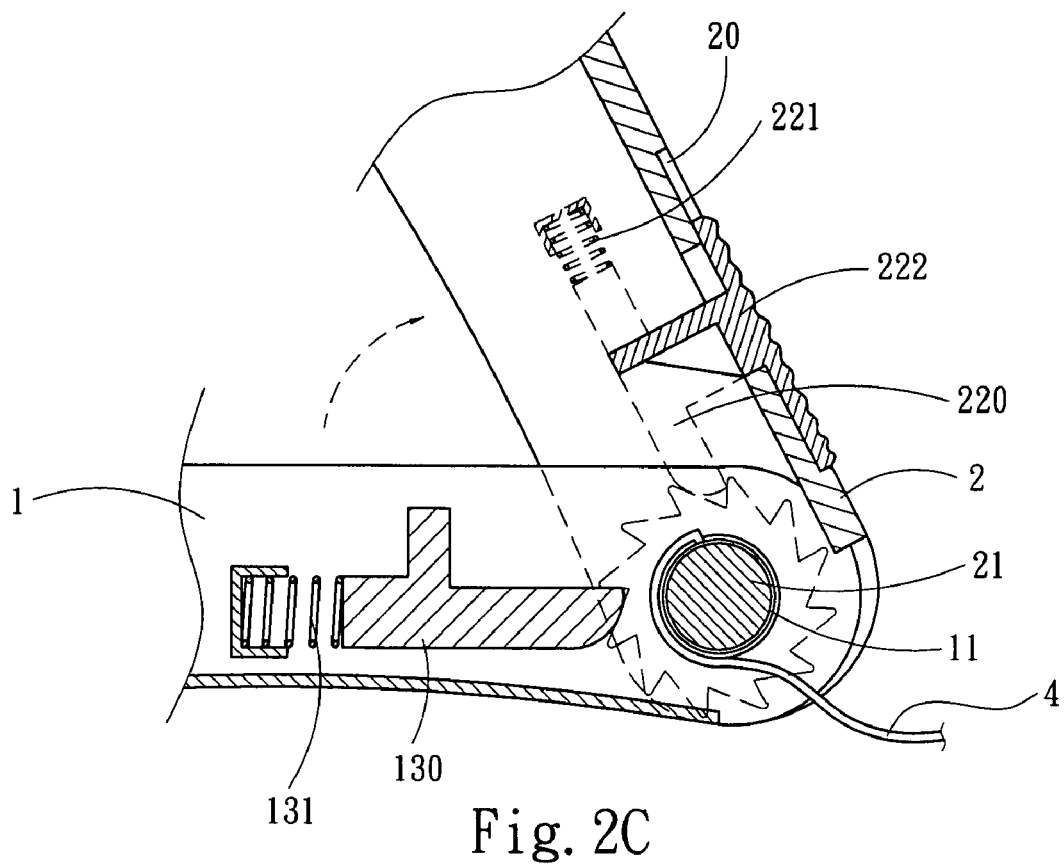
Figure 2D:
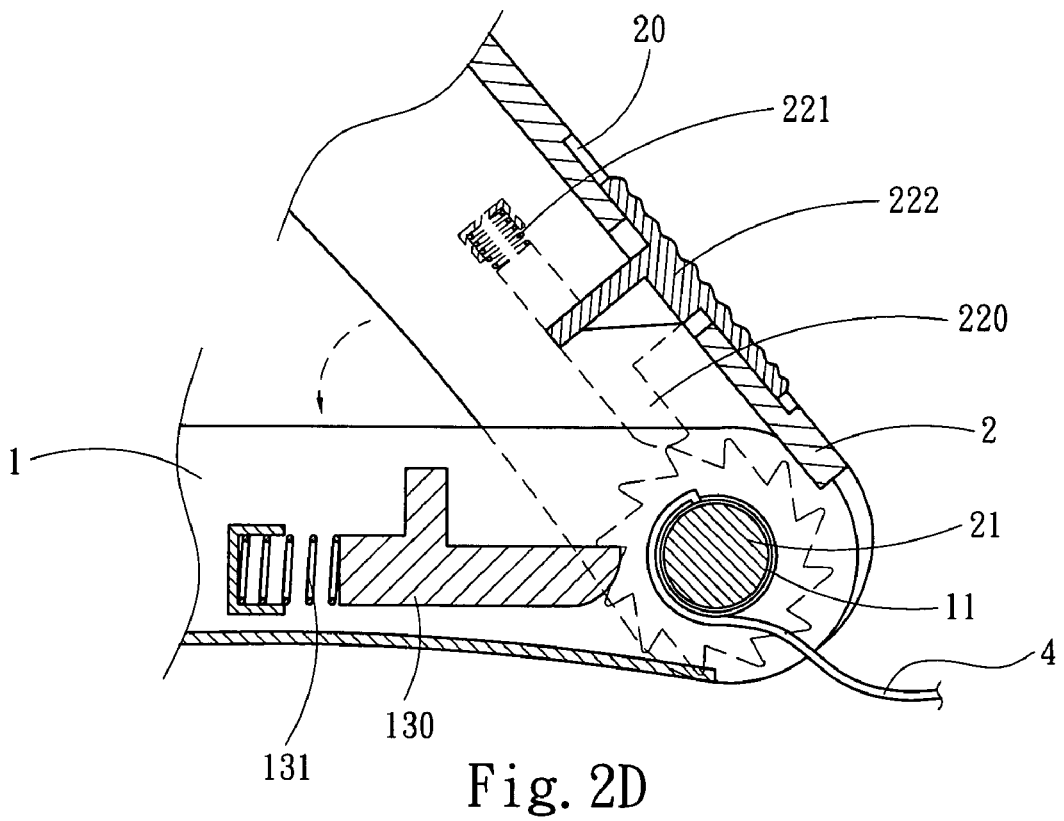

Please refer to FIG. 1, which is a decomposition drawing showing the preferred embodiment of the present invention. The belt structure includes a first housing 1, a second housing 2, a third housing 3 and a belt 4. The first housing 1 has an opening mounted at one end thereof, at least an engaging element 14 is mounted at the right and left sides of the opening, and an elastic piece 141 is mounted aside the engaging element 14 for biasing the engaging element 14. The third housing has a buckling element 31 at one end thereof which can be inserted into the opening of the first housing 1 and buckled with the engaging element 14 so as to connect the first housing 1 with the third housing 3, and the third housing also has an opening at the other end thereof for receiving therein the front end of the belt 4 and has a through hole 33 mounted thereon for extending the front end of the belt 4 out of the third housing 3. Moreover, the third housing 3 has a pressing shaft 32 mounted inside the opening thereof which can be removed in two pressing-shaft sliding troughs 34 mounted at the two sides of the third housing 3, so that when the belt 4 is pulled to have a proper length, the pressing shaft 32 can be moved to press and fix the belt 4, and preferably, the pressing shaft 32 can have some patterns on the surface thereof for increasing friction. Furthermore, a hollow axle pipe 11 and an integrally formed resisting element 130 are mounted in the space at the other end of the first housing 1, wherein two sides of the hollow axle pipe 11 have respectively mounted thereon a gear 12 and the gear 12 respectively have plural protruding teeth bent to an identical direction, the rear end of the belt 4 is fixed on the hollow axle pipe 11, and one end of the integrally formed resisting element 130 extends toward the gears 12 and engages the gears 12 and the other end thereof has an elastic element biased thereon which is preferably a spring 131 so as to provide a recovering elasticity to the resisting element 13 as it moves. The second housing 2 has an axle pillar 21 at the position corresponding to the hollow axle pipe 11, so that the axle pillar 21 can extend into the hollow axle pipe 11 for connecting and also covering the second housing 2 to the first housing 1, and the axle pillar 21 and the hollow axle pipe 11 can be the axle center for achieving an upward turning. The second housing 2 also has an integrally formed driving element 220 mounted therein, and the two sides of the second housing 2 respectively have a driving element trough 201 mounted thereon for accommodating two protruding edges respectively at the two ends of the integrally formed driving element 220, wherein the two protruding edges of the integrally formed driving element 220 are also engaged with the gears 12 through respectively one side thereof, and the other side of the protruding edge is biased by a spring 221. In addition, the integrally formed driving element 220 has a bulge mounted at the bottom thereof, and when in the normal condition, the bulge will just locate in front of the integrally formed resisting element 130. Also, a hollow trough 20 is formed at the top of the second housing 2 for exposing the sliding piece 222, which is located at the top of the integrally formed driving element 220, at the top of the second housing 2. Therefore, the first housing 1 and the second housing 2 are connected through the hollow axle pipe 111 and the axle pillar 21, the two ends of the belt 4 are respectively connected to the first housing 1 and the third housing 3, and the third housing 3 can be buckled with the first housing, thereby achieving a belt structure capable of surrounding human body. When pressing down the engaging element 14 of the first housing 1, the buckling element 31 of the third housing 3 will be released for separating the first housing 1 from the third housing 3, thereby achieving a fast buckling and loosing function.

The belt structure of the present invention also possesses the function of fine tuning of tightness, as shown in FIGS. 2A, 2B, 2C and 2D. As the first housing 1 and the second housing 2 are located at the original position, the integrally formed resisting element 130 and the integrally formed driving element 220 are simultaneously engaged with the gears 12, and when the user has the need to fine tune the tightness of the belt 4, he or she can pull up the second housing 2, and then, the integrally formed driving element 220 will also be moved owing to the movement of the second housing 2, so that the integrally formed driving element 220 will reject and move the gears 12, and since the plural protruding teeth are all bent toward one identical direction, the gears 12 can be turned along the moving direction of the integrally formed driving element 220. Then, owing to the spring 131, the integrally formed resisting element 130 can cooperate with the turning of the gears 12 to have a slightly backward movement, and when the gears 12 turn, the hollow axle pipe 11 will also turn, so that the belt 4 fixed on the hollow axle pipe 11 can be tightened. After the second housing 2 is moved, since the plural protruding teeth on the gears 12 are bent toward one identical direction, the integrally formed driving element 220 can cooperate with the spring 221 to have a slightly backward movement, and thus, the second housing 2 can go back to the original position to cover the first housing 1. At the same time, the integrally formed resisting element 130 in the first housing 1 still engage the gears 12 for maintaining the positions of the gears 12 and also the tightness of the belt 4. Therefore, through the second housing 2 being constantly pulled and homed to move the integrally formed driving element 220, the belt 4 on the hollow axle pipe 11 can be gradually tightened. A mechanism for fine tuning the tightness is formed.

Figure 3:
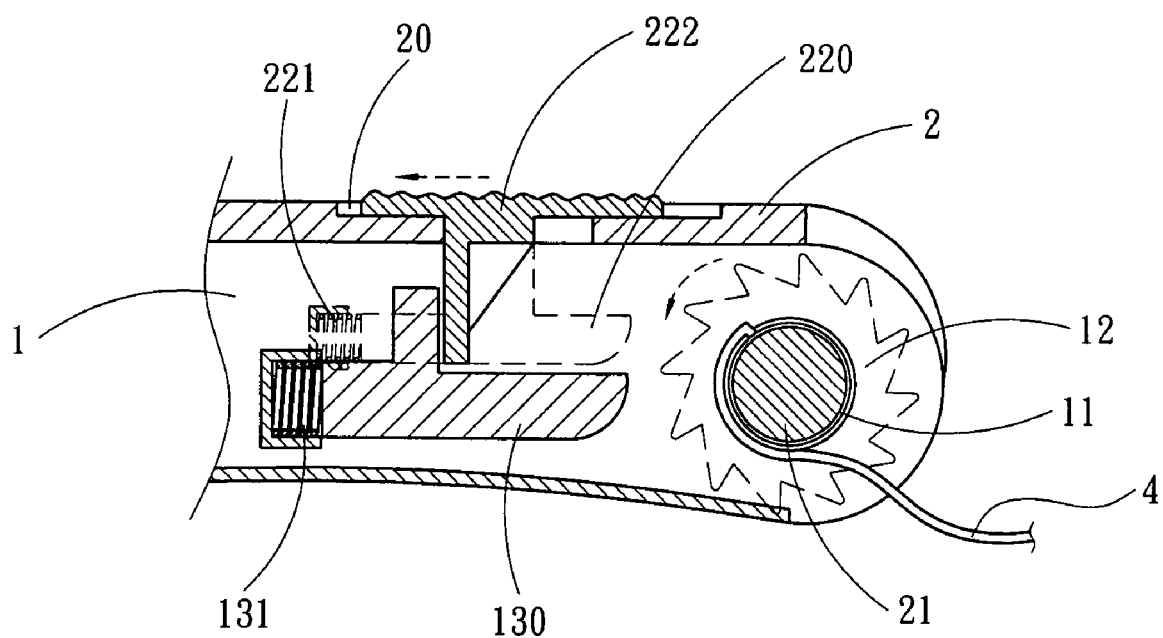
FIG. 3 is a schematic view showing the loosing of the gear.

Please refer to FIG. 3, which is a schematic view showing the loosing of the gear 12. When at the original position that the second housing 2 is covered on the first housing 1, the sliding piece 222 can be moved to move the integrally formed driving element 220, and since the bulge at the bottom of the integrally formed driving element 220 is engaged with the integrally formed resisting element 130, the integrally formed driving element 220 and the integrally formed resisting element 130 can simultaneously loose the gears 12 for turning the gears 12 and also the hollow axle pipe 11 between the gears 12 back to the original position and further loose the belt 4, so that a mechanism for fine tuning the tightness of the belt 4 and fast loosing thereof is achieved.

Figure 4:
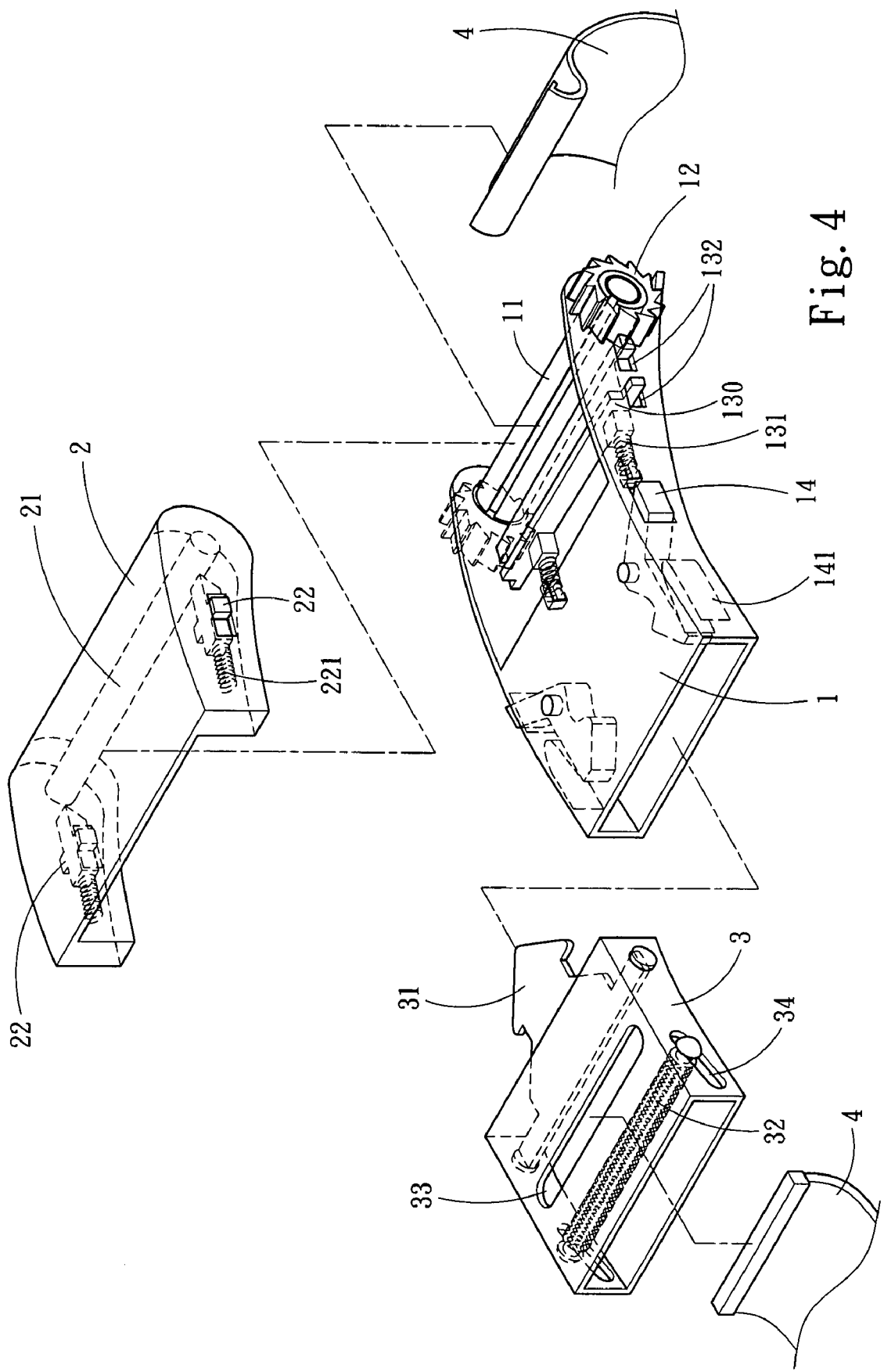
FIG. 4 is a decomposition drawing showing a second preferred embodiment according to the present invention.

Please refer FIG. 4, which shows a second embodiment of the present invention. In this embodiment, plural driving elements 22 are used to drive the gears 12. The first housing 1 has an integrally formed resisting element 130 mounted therein, which is engaged with the gears 12 located at the two sides of the hollow axle pipe 11, and the first housing also has resisting-element windows mounted at two sides thereof for exposing the integrally formed resisting element 130 out of the first housing 1. The right and the left sides of the second housing 2 respectively have a driving element 22 mounted thereon, and the driving elements 22 are also respectively engaged with the gears 12. The second housing also has driving-element window 222 formed thereon for exposing the respective protruding at one end of the respective driving element 22 out of the second housing 2, so that the driving elements 22 can be manually moved through the driving-element window 222. In this embodiment, the fine tuning is also achieved by moving the second housing 2, and for loosing the gears 12, it has to move the driving elements 22 at the same time to reject the integrally formed resisting element 130 so as to simultaneously loose the driving elements 22 and the integrally formed resisting element 130.

The elastic element for biasing the driving element 22, the integrally formed resisting element 130 and the engaging element 14 can be a spring or an elastic piece. Moreover, the first housing can be separated into two sub housings, which can be re-assembled, according to the different functions of buckling and fine tuning. Furthermore, a time alarm also can be mounted on the first, the second and the third housings. Besides, the integrally formed resisting element 130 also can be replaced by plural resisting elements to respectively engage the gears 12.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A belt structure for binding a human body for first aid, comprising:

a belt for surrounding the human body;

a first housing, wherein the first housing has a hollow axle pipe at the front section thereof for fixing the front end of the belt, at least a gear is mounted on the hollow axle pipe, the first housing has at least a resisting element mounted therein for engaging the gear, the first housing has at least a resisting-element window formed thereon for exposing the two ends of the resisting element, the first housing also has a buckling trough mounted at the rear section thereof and an engaging element mounted therein, and the resisting element and the engaging element are respectively biased by an elastic element at one end thereof;

a second housing, wherein the second housing is covered on the hollow axle pipe and the resisting element of the first housing, the second housing has an axle pillar mounted therein for extending into the hollow axle pipe, the second housing has at least a driving element mounted thereinside and an elastic element biasing the driving element, the second housing has at least a window formed thereon for exposing the driving element, each gear inside the first housing is engaged by the driving element, and the driving element has a bulge mounted thereon for engaging the resisting element as the driving element is moving backward, thereby the movement of the driving element rejects the resisting element to loose the gear; and a third housing, wherein the third housing has an opening for fixing the rear end of the belt and another opening for extending out thereof, the third housing also a pressing shaft for pressing and fixing the belt, and the third housing further has a buckling element at the other end thereof, wherein the two ends of the belt are respectively fixed at the first housing and the third housing and form a circular belt structure through the first housing and the third housing being buckled together, the second housing turns upwardly by using the axle pillar in the hollow axle pipe as the axle center so as to drive the gear by the driving element and also engaging and fixing the gear by the resisting element as the second housing is homed, and the engaging element and the buckling element respectively of the first housing and the third housing are capable of being released fast for separating the first housing and the third housing, so that a belt structure capable of being fast buckled and loosed and capable of fine tuning the level of tightness is achieved.

2. The belt structure as claimed in claim 1, wherein the resisting element is an integrally formed resisting element.

3. The belt structure as claimed in claim 2, wherein the bulge of the driving element is toward one side of the integrally formed resisting element, so that when the driving element is moving backward, the bulge of the driving element backwardly engages the two exposed ends of the resisting element, thereby the driving element and the resisting element simultaneously loose the gear so as to loose the belt.

4. The belt structure as claimed in claim 3, wherein the driving element is an integrally formed driving element.

5. The belt structure as claimed in claim 4, wherein the integrally formed driving element in the second housing engages each gear, and the second housing has an opening at the top thereof for exposing the integrally formed driving element.

6. The belt structure as claimed in claim 1, wherein the second housing has a driving element respectively at the right side and the left side thereof.

7. The belt structure as claimed in claim 6, wherein the first housing has a resisting element respectively at the right side and the left side thereof.

8. The belt structure as claimed in claim 1, wherein the bulges of the driving elements are toward one side of the resisting element, so that when the driving elements are moving backward, the bulges of the driving elements backwardly engages the respective two exposed ends of the resisting elements, thereby the driving elements and the resisting elements simultaneously loose the gear so as to loose the belt.

9. The belt structure as claimed in claim 1, wherein the resisting element and the driving element simultaneously engage the gear, and when the second housing moves upward by taking the axle pillar and the hollow axle pipe as the axle center, the driving element also is moved to drive the turning of the gear and the hollow axle pipe, thereby tightening the belt on the hollow axle pipe and also achieving a fine tuning mechanism.

10. The belt structure as claimed in claim 1, wherein the first housing has a buckling trough mounted at the rear section thereof for receiving the buckling element of the third housing, and the engaging element disposed in the buckling trough is buckled with the buckling element so as to connect the first and the third housings together.

11. The belt structure as claimed in claim 1, wherein through pressing the engaging element of the first housing to release the buckling element, the first housing and the third housing, which are originally buckled together, are separable.

12. The belt structure as claimed in claim 1, wherein the plural protruding teeth on the gear are bent toward one identical direction.

13. The belt structure as claimed in claim 1, wherein the elastic element for rejecting to the driving element, the resisting element and the engaging element is a spring.

14. The belt structure as claimed in claim 1, wherein the elastic element for biasing the driving element, the resisting element and the engaging element is an elastic piece.

15. The belt structure as claimed in claim 1, wherein the pressing shaft of the third housing further comprises patterns on the surface thereof for increasing friction, and the two ends thereof are exposed out of the third housing and manually moved to press and fix the belt.

16. The belt structure as claimed in claim 1, wherein the first housing is capable of being separated into two sub housings, which can be re-assembled, according to the different functions of buckling and fine tuning.

17. The belt structure as claimed in claim 1, wherein a time alarm is further mounted on the first housing, the second housing and the third housing.

* * * * *